(12) United States Patent
Kleven

(10) Patent No.: US 10,828,514 B2
(45) Date of Patent: Nov. 10, 2020

(54) RADIOTHERAPY SYSTEM PREVENTING RADIATION OF HEALTH TISSUE

(71) Applicant: PH Kleven AS, Kongsberg (NO)

(72) Inventor: Per Havard Kleven, Kongsberg (NO)

(73) Assignee: PH Kleven AS, Kongsberg (NO)

(*) Notice: Subject to any disclaimer, the term of this patent is extended or adjusted under 35 U.S.C. 154(b) by 63 days.

(21) Appl. No.: 16/330,106

(22) PCT Filed: Sep. 12, 2017

(86) PCT No.: PCT/IB2017/055487
§ 371 (c)(1),
(2) Date: Mar. 4, 2019

(87) PCT Pub. No.: WO2018/047142
PCT Pub. Date: Mar. 15, 2018

(65) Prior Publication Data
US 2019/0232089 A1 Aug. 1, 2019

(30) Foreign Application Priority Data

Sep. 12, 2016 (SE) ...................... 1651223

(51) Int. Cl.
*A61N 5/10* (2006.01)
(52) U.S. Cl.
CPC ......... *A61N 5/1084* (2013.01); *A61N 5/1049* (2013.01); *A61N 5/1065* (2013.01); *A61N 2005/1087* (2013.01)
(58) Field of Classification Search
CPC .. A61N 5/1048; A61N 5/1049; A61N 5/1064; A61N 5/1065; A61N 5/1077; A61N 5/1084; A61N 2005/1087
See application file for complete search history.

(56) References Cited

U.S. PATENT DOCUMENTS

| 5,528,651 A | 6/1996 | Leksell et al. |
| 2004/0005027 A1 | 1/2004 | Nafstadius |

(Continued)

FOREIGN PATENT DOCUMENTS

| EP | 1741469 A1 | 1/2007 |
| WO | WO00/54689 A | 9/2000 |

(Continued)

*Primary Examiner* — Thomas R Artman
(74) *Attorney, Agent, or Firm* — Christian D. Abel

(57) ABSTRACT

A radiotherapy system comprising a plurality of particle beam sources (1a, 1b, 1c) arranged to radiate particle beams (6a, 6b, 6c) on a three-dimensional radiation target (3) located inside the body of a radiotherapy patient (4), the position in space and alignment of which particle beam sources are individually controllable; and an imaging system (2) arranged to monitor the position and orientation in space of the three-dimensional radiation target including direction and speed of any movement of the radiation target, and also to monitor tissue characteristics of body tissue (5) surrounding the radiation target located in the radiation paths of the particle beams. The radiotherapy system comprises a particle beam control system (7) which, during a radiation treatment session, is arranged for receiving information on the position and orientation of the radiation target and on said tissue characteristics from the imaging system; based on the received information on said tissue characteristics, identifying body tissue which shall not be exposed to the particle beams; and in response to movement of the radiation target and/or of body tissue surrounding the radiation target, adjusting the individual positions and alignments of the particle beam sources and the individual characteristics of the particle beams so that (i) Bragg peaks or spread out Brag peaks (SOBP) of the particle beams are brought to intersect in a predetermined beam intersect region (8) inside the radiation target; and (ii) the radiation paths of the particle (Continued)

beams do not travel through said body tissue identified as not to be exposed to the particle beams.

9 Claims, 2 Drawing Sheets

(56) References Cited

U.S. PATENT DOCUMENTS

| | | |
|---|---|---|
| 2004/0024300 A1 | 2/2004 | Graf |
| 2005/0197564 A1 | 9/2005 | Dmpsey |
| 2007/0034812 A1 | 2/2007 | Ma |
| 2009/0024225 A1 | 1/2009 | Stubbs |
| 2009/0088625 A1 | 4/2009 | Oosting et al. |
| 2010/0220915 A1 | 9/2010 | Sommer |
| 2011/0240874 A1 | 10/2011 | Iwata |
| 2013/0058460 A1 | 3/2013 | Weigand et al. |
| 2015/0112197 A1 | 4/2015 | Bharat |
| 2015/0182760 A1 | 7/2015 | Raleigh |
| 2019/0175945 A1* | 6/2019 | Yan ................. A61N 5/1067 |
| 2019/0232089 A1* | 8/2019 | Kleven ............. A61N 5/1049 |

FOREIGN PATENT DOCUMENTS

| | | |
|---|---|---|
| WO | WO02/19908 A1 | 3/2002 |
| WO | WO2008/0002781 A1 | 1/2008 |
| WO | WO2015/150575 A | 10/2015 |
| WO | WO2016/014972 A1 | 1/2016 |

* cited by examiner

RADIOTHERAPY SYSTEM PREVENTING RADIATION OF HEALTH TISSUE

FIELD OF THE INVENTION

The present invention relates to radiation therapy and more specifically how to increase the effect of radiation with the goal of destroying DNA of cells in a cancer tumour with minimum damage inflicted on surrounding tissue.

In particular, the present invention relates to a radiotherapy system comprising:
 a plurality of particle beam sources arranged to radiate particle beams on a three-dimensional radiation target located inside the body of a radiotherapy patient, the position in space and alignment of which particle beam sources are individually controllable; and
 an imaging system arranged to monitor the position and orientation in space of the three-dimensional radiation target, including direction and speed of any movement of the radiation target, and also to monitor tissue characteristics of body tissue surrounding the radiation target located in the radiation paths of the particle beams.

BACKGROUND

Cancer treatment using radiotherapy involves applying ionising radiation to a patient so that radiation energy is deposited in malignant cells of the patient's body. If sufficient amount of energy is deposited, disruption of DNA and the subsequent death of the radiated cells result.

Protons and other charged particles display a depth-dose curve which is suitable for radiation therapy. Such radiation produces a so-called Bragg peak—a sharp increase in the deposited energy in the very last region of the trajectory of the charged particle—where charged particle loses its whole energy and the deposited dose falls to zero. By adding Bragg peaks that are shifted in depth and weighted, a 'spread-out Bragg peak' (SOBP) can be created.

US 2016/0144201 A1 discloses a system for intensity-modulated proton therapy in which multiple proton beams are delivered to a patient from multiple directions and angles. The system can control, configure, or select energy distributions of the proton beams, and also dynamically change the positions and/or alignments of the beams.

US 2016/0144201 A1 also discloses method of creating a proton treatment plan comprising the steps of dividing volumes of interest into sub-volumes, applying dose constraints to the sub-volumes based on, inter alia, patient movement, finding one or more feasible configurations of the proton therapy system, and selecting a proton beam configuration that improves or optimizes one or more aspects of the proton therapy.

However, a problem associated with the proton therapy system of US 2016/0144201 A1, and other prior art radio therapy systems, is that patient movement during treatment makes it difficult for the system to accurately deliver the radiation dose to the intended position within the radiation target. In fact, even if the patient is restrained, organ movements within the patient's body will still make it difficult for prior art radiation therapy systems to accurately deliver the radiation dose, as will motions resulting from breathing and involuntary muscular activity, e.g. heart beats.

Therefore, when preparing a treatment plan using prior art systems, dose constraints need to take into account the uncertainty associated with patient and/or organ movements during treatment. In practise, this uncertainty may result in that the operator of the system sets the system to deliver a lower overall dosage to avoid damaging healthy tissue. This, in turn, may result in a less efficient therapy than if the uncertainty did not exist.

An object of the present invention is to mitigate this problem and provide a radiotherapy system which provides more certainty with regards to patient and/or organ movements during treatment.

SUMMARY OF THE INVENTION

The radiotherapy system according to the invention is characterised in that it comprises:
 a particle beam control system which, during a radiation treatment session, is arranged for:
  receiving information on the position and orientation of the radiation target and on said tissue characteristics from the imaging system;
  based on the received information on said tissue characteristics, identifying body tissue which shall not be exposed to the particle beams; and
  in response to movement of the radiation target, adjusting the individual positions and alignments of the particle beam sources and/or the individual characteristics of the particle beams so that:
   (i) Bragg peaks or spread out Brag peaks (SOBP) of the particle beams are brought to intersect in a predetermined beam intersect region inside the radiation target; and
   (ii) the radiation paths of the particle beams do not travel through said body tissue identified as not to be exposed to the particle beams.

Consequently, the invention is based on using a particle beam control system to simultaneously and in a coordinated fashion operate a plurality of particle beam sources arranged to radiate particle beams. The particle beam control system is arranged to determine and control positions and alignments of the particle beam sources and the characteristics of the particle beams to control said beams so that they intersect and present their Bragg peaks, or their spread out Bragg peaks (SOBP), in a predetermined beam intersect region within a radiation target, e.g. a cancer tumour, while simultaneously preventing the particle beams from traveling through body tissue which has been identified as not to be exposed to the particle beams.

Prior to a treatment session, a treatment plan is established stating the required irradiation dose to be delivered to each part or region of the radiation target, as well as the radiation dose to be delivered to the radiation target from different directions. The treatment plan is typically created based on a detailed visualization of the radiation target and surrounding tissue, e.g. organs, bones and other tissue structures. The treatment plan typically also identifies body tissue and/or regions within the patient's body which are not to be exposed to the particle beams.

During a treatment session, the position and alignment of each particle beam source are adjusted in response to movement of the radiation target and/or movement of the surrounding tissue to find, at every point in time, a radiation path or trajectory of each particle beam that presents the Bragg peak, or the spread out Bragg peak (SOBP), in the intended beam intersect region while avoiding sensitive regions or structures in the patient's body which, e.g. according to a treatment plan, shall not be exposed to the particle beam (e.g. structures of the central and/or peripheral nervous system, eyes, organs identified not to be irradiated etc.) and/or regions or structures within the patient's body which may have unwanted effects on the particle beam (e.g. bones). If a suitable particle beam trajectory cannot be found for a particle beam source, the particle beam source may temporarily be shut down.

Movement of the radiation target and/or movement of the surrounding tissue prompting repositioning and realignment of the particle beam sources may typically be due to the patient moving or due to movement of internal organs of the patient.

If the radiation target is large, the treatment plan may call for the beam intersect region to be swept across the radiation target. Consequently, the position and alignment of each particle beam source may then be adjusted to effectuate such a sweeping action. In such a case, repositioning and realignment of the particle beam sources to achieve the sweeping action may be combined with repositioning and realignment of the particle beam sources to account for movement of the radiation target and/or movement of the surrounding tissue.

The imaging system may comprise an X-ray computed tomography (X-ray CT) imaging system, a magnetic resonance imaging (MRI) system, a proton computed tomography (PCT) imaging system, a positron emission tomography (PET) system, or any other type of imaging system, or combination thereof, capable of providing a basis for a real time, or a near-real time, representation of the intended target and tissue surrounding the intended target which is located in the radiation paths of the particle beams.

The real time, or a near-real time, representation of the target and surrounding tissue may be based on a static representation of the target and surrounding tissue and on knowledge of motion patterns together with tracking of motion to align and update the representation in real time. The real time tracking of motion can be accomplished by the use of ultrasound or other already known means, e.g. as is disclosed in U.S. Pat. No. 5,207,223 and WO 02/19908 A1.

Based on said representation provided by the imaging system, the positions and alignments of the particle beam sources and the modulations of the particle beams can be adjusted to dynamically compensate for movements of the radiation target and surrounding tissue so that the Bragg peaks or spread out Brag peaks (SOBP) of the particle beams are maintained intersecting in the predetermined beam intersect region inside the radiation target, while at the same time establishing radiation paths of the particle beams which do not travel through body tissue identified as not to be exposed to the particle beams. In this way a more efficient dose delivery can be achieved, thus improving the effect of the radio therapeutic treatment inside the tumour and, at the same time, reducing the radiation dose delivered to surrounding, healthy tissue.

Due to the capability of the particle beam control system to reposition and control the particle beams, the system according to the invention can be used to treat large tumours by sweeping the beam intersect region across the tumour while simultaneously compensating for movements of the radiation target and surrounding tissue. Due to the same capability, the system according to the invention can also be used to treat a plurality of tumours during a treatment session.

The system according to the invention can be used to document, electronically and in real time, a complete treatment session, e.g. document the accumulated radiation dose in each part of the target or targets and the system set-up used during the treatment session.

The radiotherapy system according to the invention may comprise one or more particle generators or accelerators for producing the particle beams and providing them to the particle beam sources, each of which accelerators may be configured to generate one or more particle beams or beamlets. Alternatively, each beam source may be capable of producing its own particle beam or beamlets.

Consequently, the term "particle beam source" does not necessarily imply that the particles are generated at the particle beam source, but is understood to define a starting point of a linear path along which the particle beam travels before reaching the radiation target. In other words, a particle beam source can be viewed upon as a beam exit or nozzle having a unique position in space and alignment, from which beam exit or nozzle the particle beam travels linearly to the radiation target. However, as previously stated, each particle beam source may be supplied by particles from the same particle generator.

The particle beams may be proton beams.

In the following, the term "particle beam" is understood to mean one or a plurality of particle beams or beamlets emerging from one and the same particle source and having the same beam path, unless otherwise stated or implicitly understood from the context. For example, the particle beam may be of the type which is referred to within the industry as a "pencil beam". Alternatively, an existing, new technology for real-time adjustment of the contour of a particle beam can be applied. This new technology is called image-guided radiation therapy (IGRT) or four-dimensional radiation therapy.

For each particle beam source, the radiotherapy system may comprise actuators which are capable of controlling the position and alignment of the beam source.

If the particle beam is a proton beam, the trajectory of the particle beam is normally manipulated by permanent magnets or electromagnets, and there will normally be large demands on power delivery and cooling in such an actuator system. For example, cooling may be required for energy transport or to provide conditions for superconductivity, and the actuator system may have to be designed to handle large and heavy objects with high energy input. The actuators which control the position and alignment of the beam source may be constructed by devices controlling the source by mechanically shifting the beam guidance system or by controlling the beam guidance system by electrically adjusting the magnetic fields. The two methods for beam manipulation can be combined.

In combination with each particle beam source, the radiotherapy system may also comprise beam modulating devices which are configured to modulate the characteristics of the particle beam, e.g. beam cross-sectional area, beam energy and beam frequency, e.g. by adjusting an attenuator positioned in the beam path of at least one of the particle beams, e.g. by dynamically inserting and withdrawing one or a plurality of attenuators in the beam path or portion thereof. It may be advantageous if the modulating device is arranged to interact with the particle beam after the particle beam leaves the particle beam source. However, a modulating device may interact with the particle beam at any stage after the generation of the beam.

By individually controlling the position and alignment of the beam sources and the beam modulation, i.e. the characteristics of the particle beam, the particle beam control system ensures that the Bragg peaks or the SOBP are focused in the beam intersect region.

The particle beam control system may be configured to control the start and stop of individual particle beams, and also the length in time during which each particle beam irradiates the beam intersect region.

The particle beam control system may control the particle beams in such a way that the volume in space occupied by the beam intersect region is relatively large, in which case the beam intersect region may encompass the entire radiation target, at least if the radiation target is small. Alternatively, the particle beam control system may be arranged to focus the particle beams such that the volume occupied by the beam intersect region becomes small, in which case the delivered radiation is concentrated to this small volume.

If the radiation target is larger than the volume occupied by the beam intersect region, the beam intersect region may be brought to swept or scan over the radiation target to deliver the desired irradiation dose to different parts of the radiation target. Such sweeping or scanning may be stepwise or continuous.

In order to dynamically control the beam intersect region, the position and alignment of each particle beam source must be controlled dynamically. Variables providing such control may be referred to as "beam positioning variables" and comprise five variables per particle beam source: three variables defining the position of the particle beam source, e.g. represented by Cartesian coordinates x, y, y, and two variables defining pitch and yaw of the particle beam, e.g. as represented by angles of rotation measured about orthogonal pitch and yaw axes. Information on the third orientation coordinate, roll, is normally not necessary since rotation of the particle beam source about the beam axis will not affect the position of the Bragg peak or SOBP.

In order to dynamically control the characteristics of the particle beams, the particle beam control system may control variables such as, for example, beam energy, beam frequency and beam attenuation. Variables providing such control may be referred to as "beam characteristics variables". Of these variables, the attenuation of the beam are the one most suitable for dynamic control as it can be controlled by dynamically inserting and removing attenuators in the path of the particle beam.

The objective of adjusting "beam positioning variables" and "beam characteristics variables", is to secure an exact positioning of the occurrence of the Bragg peak or SOBP of each particle beam, so that it occurs exactly in the predefined beam intersect region, i.e. so that the Bragg peaks or SOPB of the particle beams are brought to intersect in the beam intersect region. The extent of the beam intersect region is generally determined by the cross-sectional areas of the intersecting particle beams and the axial extent of their Bragg peaks. If the Bragg peak is defined as the region where deposited energy is more than 80% of maximum deposited energy, the volume of the beam intersect region can typically be set to be within the range of 50 to 1000 $mm^3$, depending on the individual cross-sectional areas of the particle beams and the angles between the particle beams.

The position of individual particle beams in the beam intersect region should normally be set to be within an accuracy of +/−0.5 mm, and in order to provide sufficient dynamic properties, the actuators controlling the position and alignment of the particle beam sources should normally be set to be able to operate at speed of at least 20 mm/s and be able to accelerate at an acceleration of at least 40 $mm/s^2$. The actuators may comprise electrical motors and associated control systems.

The imaging system is arranged to continuously monitor the position and orientation in space, i.e. attitude, of the target as well as velocity data, i.e. data on changes in the position and attitude of the target. The imaging system is also arranged to monitor tissue surrounding the target, in particularly information on the tissue lying in the path of the particle beams.

Based on this data, the imaging system can dynamically map the tumour and the surrounding tissue and construct a mathematical model representing the relevant part of the patient's body. Different types of tissue (bone, flesh, organs, tumour etc.) will be mapped and using information on how the different types of tissue interact with the particle beams, the particle beam control system will be able to continuously adjust the position and alignment of each particle source, and the characteristics of its particle beam, i.e. the above-discussed "beam positioning variables" and "beam characteristics variables", so that the beam intersect region is locked to the intended position. The set-up of the particle beam sources and their application, i.e. the irradiation activity and its calculated effect, may advantageously be mapped using the same mathematical model, so that the actual real time irradiation as well as the accumulated effect in different parts of the body are registered, e.g. in each cubic mm (or per larger or smaller units, as chosen).

The information monitored by the imaging system is forwarded to the beam control system which processes the information and automatically calculates and implements, dynamically, the optimum combination of beam source positions, beam source alignments and beam modulations to focus and maintain the beams on the beam intersect region. When the beam intersect region is moving, e.g. when the beam intersect region in intended to sweep over the target and/or when the beam intersect region is to follow the target when the target is moving, e.g. due to breathing motion, it will sometimes be necessary to dynamically move individual particle beam sources in order for the trajectories of the beams to avoid bone, such as ribs, as bone has a different and normally unwanted effect on the particle beam. This is another reason why it is necessary to dynamically control five axis per particle beam source instead of two.

Adjusting the "beam positioning variables" and "beam characteristics variables" may comprise applying a range shifter so that the distal position of the Bragg peak or SOBP can be controlled to occur in the beam intersect region, e.g. as is described in PCT/US2008/055069, which is hereby incorporated by reference.

The energy loss for a beam of charged particles varies substantially, as measured per millimetre, depending upon the category of tissue it will pass through before reaching the beam intersect region in the target. Whether it will pass through air, flesh, various organs, or bone tissue, and the path distance of each of these, will have a profound effect on at which distance from the beam source the Bragg peak or SOPB will occur.

Taking into account the relevant type of particles in the particle beams and other relevant beam characteristics, the mathematical model of the target and surrounding tissue can be furnished with data showing energy loss per mm per category of tissue. In this respect, 3D dose tracking may be applied, e.g. as is described in U.S. Pat. No. 9,199,093, which is hereby incorporated by reference.

In the following, the invention will be discussed in more detail with reference to the appended drawings.

DETAILED DESCRIPTION OF THE INVENTION

When a charged particle moves through matter, it ionizes atoms of the material and deposits a dose along its path. As the velocity of the charged particle decreases, the deposited energy increases. For protons, a-rays, and other ion rays, the deposited energy peaks immediately before the particles come to rest and, consequently, if the energy loss of such ionizing radiation is plotted as a function of distance travelled through matter, the resulting curve will display a pronounced peak, as so called Bragg peak, immediately before the deposited energy becomes zero.

Figure 1:
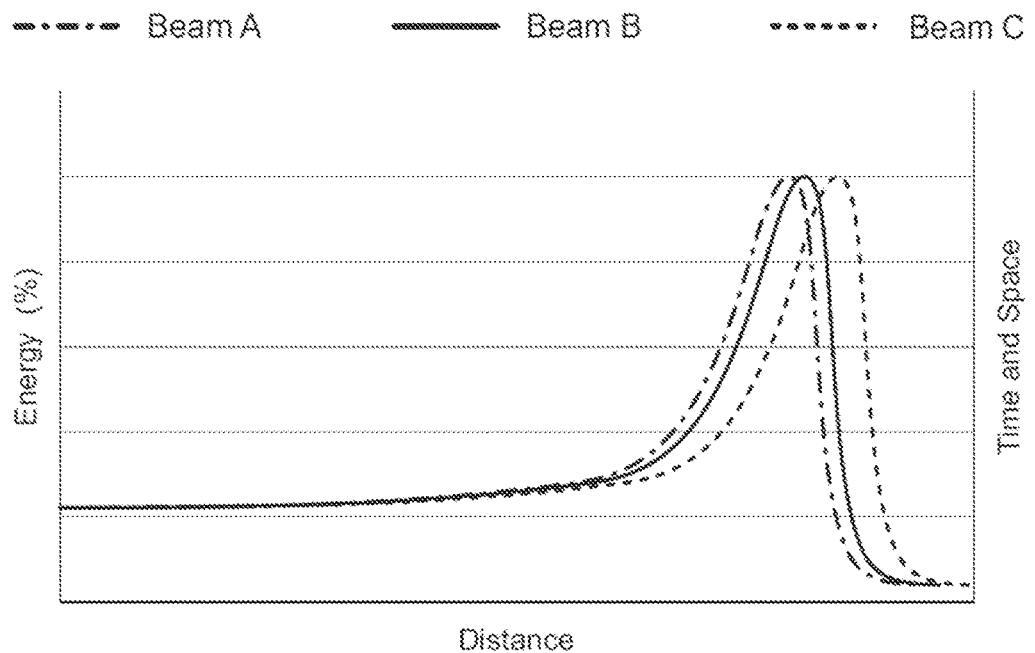
FIG. 1 illustrates Bragg peaks of three different particle beams.

This is illustrated in FIG. 1 which discloses Bragg peaks from three different particle beams.

Figure 2:
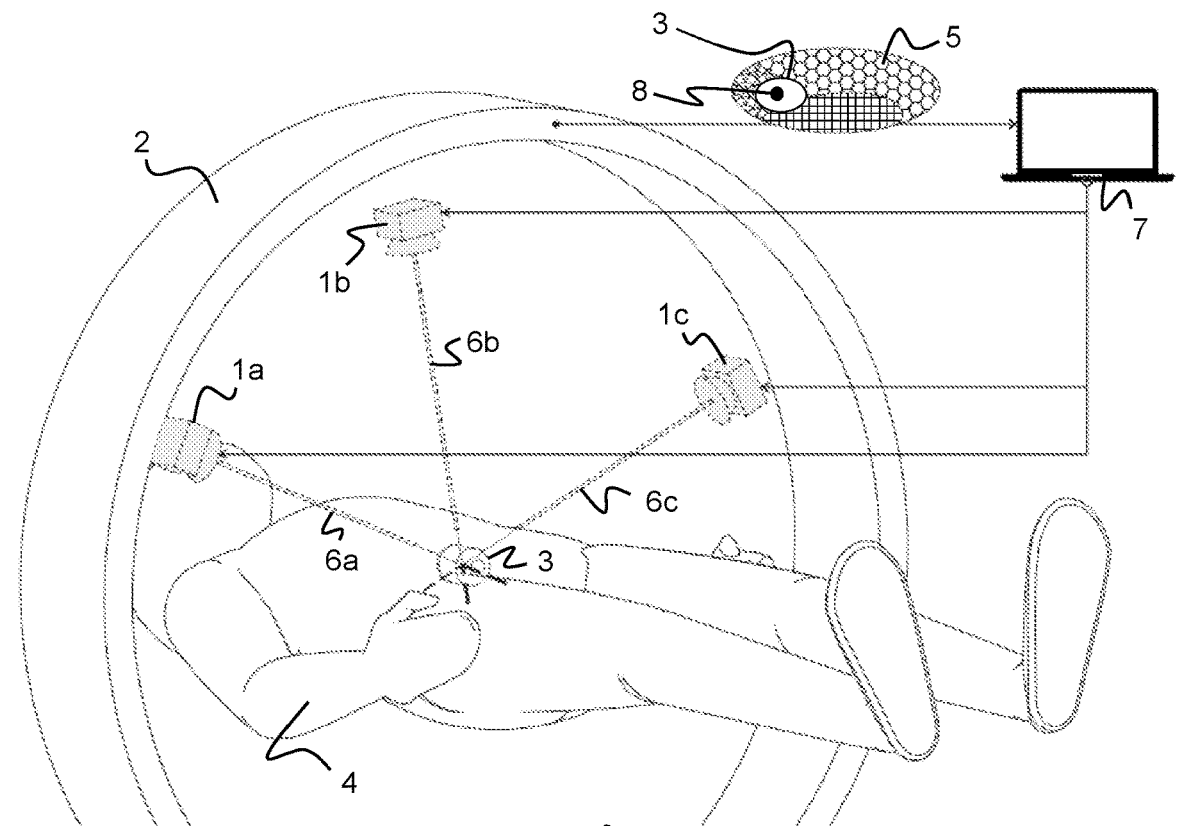
Figure 3:
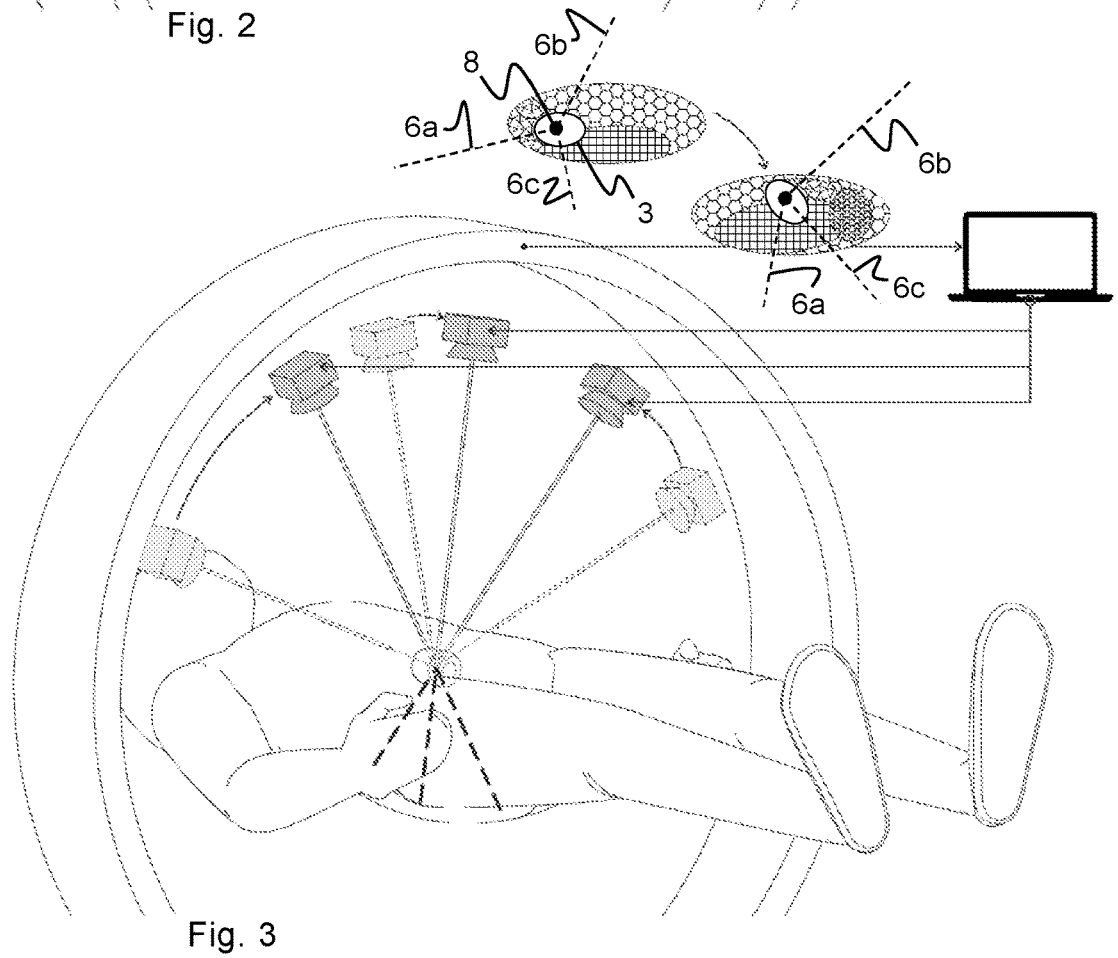

FIGS. 2 and 3 disclose an embodiment of a radiotherapy system according to the invention. The radiotherapy system comprises a plurality of particle beam sources 1a-1c which are arranged to radiate particle beams 6a-6c on a three-dimensional radiation target 3 located inside the body of a radiotherapy patient 4.

The radiotherapy system also comprises a particle beam control system 7 which is arranged to individually control the position in space and the alignment of the particle beam sources 1a-1c as well as the characteristics of each individual particle beam so that the Bragg peaks or spread out Brag peaks (SOBP) of the particle beams 6a-6c are brought to intersect in a predetermined beam intersect region 8 inside the radiation target 3 during a radiation treatment session.

This control comprises controlling three variables defining the position of each particle beam source, e.g. represented by Cartesian coordinates x, y, y, and two variables defining the pith and yaw of the particle beam originating from the beam source, e.g. as represented by angles of rotation measured about orthogonal pitch and yaw axes. Repositioning and/or realignment of the beam sources are effectuated using actuators, e.g. stepping motors (not disclosed).

This control also comprises controlling at least one of the energy, frequency and attenuation of each particle beam 6a-6c. For example, the control may comprise dynamically inserting and removing one or a plurality of attenuators (not disclosed) in the path of a particle beam 6a-6c between the beam source 1a-1c and the patient 4. However, if the beam sources 1a-1c are supplied with particles from a common particle generator, the particle beams may also, or alternatively, be manipulated before reaching the individual beam sources 1a-1c.

The radiotherapy system further comprises an imaging system 2 which is arranged to monitor the position and orientation in space of the three-dimensional radiation target 3, and also to monitor tissue characteristics of body tissue 5 surrounding the radiation target 3 located in the radiation paths of the particle beams 6a-6c. Based on the monitored data, the imaging system is arranged to dynamically map the target 3 and the surrounding tissue 5 and construct a mathematical model representing the relevant part of the patient's body, i.e. the target 3 and the surrounding tissue 5 lying between the target 3 and the particle beam sources 1a-1c. In this mapping, different types of surrounding tissue (bone, flesh, organs, etc.) are mapped and known information on how the different types of tissue interact with the particle beams is used to produce the mathematical model, in particular information on how much different types of tissue attenuate the particle beams.

In operation, the imaging system 2 monitors the position and orientation in space of the target 3 and surrounding tissue 5, and continuously updates the map of the target 3 and the surrounding tissue 5 and as well as the mathematical model representing the relevant part of the body of the patient 4. The updated map and/or the updated mathematical model is forwarded to the particle beam control system 7.

The particle beam control system 7 processes the information received from the imaging system 2 and, based on this information, produces control signals which reposition and/or realign the particle beam sources and/or changes the characteristics of the particle beams 6a-6c so that the Bragg peaks or spread out Bragg peaks (SOBP) of the particle beams 6a-6c are maintained within the intended beam intersect region 8, taking into account any change of position and/or attitude of the target 3.

Figure 4:
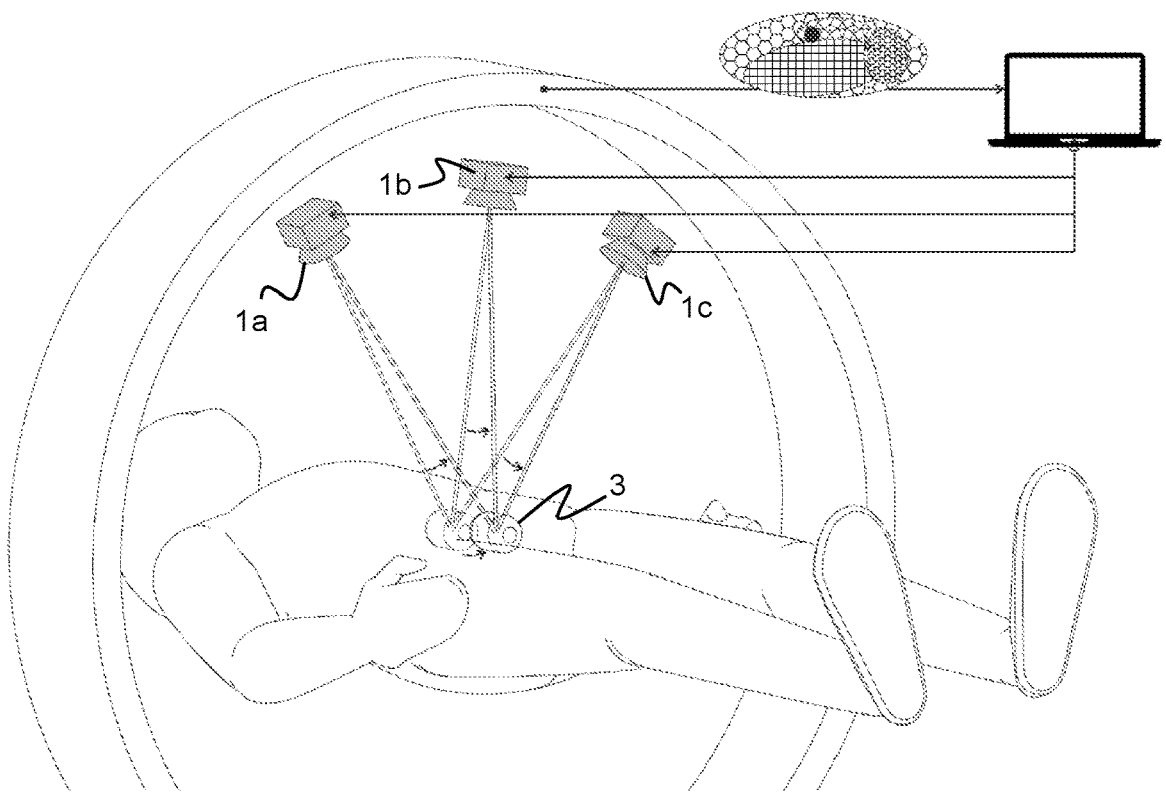
FIGS. 2 to 4 disclose an embodiment of a radiotherapy system according to the invention.

This is illustrated in FIGS. 3 and 4, where a change in position and/or orientation in space of the target 3, e.g. due to the patient or internal organs of the patient moving, prompts the particle beam control system 7 to reposition and realign the beam sources 1a-1c. If the change of position and/or orientation in space of the target is small, the beam sources 1a-1c may not necessarily need be repositioned, but merely realigned. Such a situation is illustrated in FIG. 4.

From the information received from the imaging system 2, the particle beam control system 7 also identifies body tissue which, according to the treatment plan, shall not be exposed to the particle beams 6a-6c. When repositioning and realigning the beam sources 1a-1c, the particle beam control system 7 ensures that such body tissue is not exposed to the particle beams 6a-6c.

Repositioning and realignment of the beam sources 1a-1c may not necessarily be triggered by a movement of the radiation target, but may be triggered by a movement causing body tissue not to be exposed to the particle beam 1a-1c to be brought into the radiation paths of the particle beams 6a-6c. For example, a rotation of the patient's body leaving the radiation target essentially in the same location in space, may nevertheless require one or a plurality of the beam sources 1a-1c to be repositioned and/or realigned if the rotation brings body tissue not to be irradiated into the radiation path of a particle beam 6a-6c.

If the particle beam control system 7 cannot find a "safe" radiation path for a particle beam source 1a-1c, i.e. a radiation path avoiding body tissue not to be exposed to the particle beams, the particle beam source may have to be shut down until such a radiation path is found, e.g. until the radiation target and surrounding tissue are shifted so that such a radiation path becomes available again.

The intended beam intersect region 8 may be locked to a given position in the target 3, as is disclosed in FIGS. 2 and 3. Alternatively, the beam intersect region 8 may be arranged to sweep over the target 3, continuously or stepwise, in which case the beam control system 7 must also take into account the new position of the beam intersect region when repositioning and/or realigning the beam sources 1a-1c in addition to compensating for any change in position and/or orientation in space of the target and for any change in the composition of the tissue lying in the paths of the particle beams 6a-6c.

In the preceding description, various aspects of the apparatus according to the invention have been described with reference to the illustrative embodiment. For purposes of explanation, specific numbers, systems and configurations were set forth in order to provide a thorough understanding of the apparatus and its workings. However, this description is not intended to be construed in a limiting sense. Various modifications and variations of the illustrative embodiment, as well as other embodiments of the apparatus, which are apparent to persons skilled in the art to which the disclosed subject matter pertains, are deemed to lie within the scope of the present invention a defined by the following claims.

The invention claimed is:

1. A radiotherapy system comprising:
 a plurality of particle beam sources arranged to radiate particle beams on a three-dimensional radiation target located inside the body of a radiotherapy patient, the position in space and alignment of which particle beam sources are individually controllable; and
 an imaging system arranged to monitor the position and orientation in space of the three-dimensional radiation target including direction and speed of any movement of the radiation target, and also to monitor tissue characteristics of body tissue surrounding the radiation target located in the radiation paths of the particle beams;
wherein the radiotherapy system comprises:
 a particle beam control system which, during a radiation treatment session, is arranged for:
  receiving information on the position and orientation of the radiation target and on said tissue characteristics from the imaging system;
  based on the received information on said tissue characteristics, identifying body tissue which shall not be exposed to the particle beams; and
  in response to movement of the radiation target and/or of body tissue surrounding the radiation target, adjusting the individual positions and alignments of the particle beam sources and/or the individual characteristics of the particle beams so that:
  Bragg peaks or spread out Brag peaks of the particle beams are brought to intersect in a predetermined beam intersect region inside the radiation target; and
  the radiation paths of the particle beams do not travel through said body tissue identified as not to be exposed to the particle beams.

2. The radiotherapy system according to claim 1, wherein the individual characteristics of the particle beams comprise at least one of: particle beam energy; particle beam frequency; and particle beam attenuation.

3. The radiotherapy system according to claim 2, wherein the particle beam control system is arranged to dynamically adjust an attenuator positioned in the beam path of at least one of the particle beams.

4. The radiotherapy system according to claim 1, wherein the position in space and alignment of the particle beam sources are individually controlled by actuators controlled by the particle beam control system.

5. The radiotherapy system according to claim 1, wherein the imaging system comprises any one of an X-ray computed tomography, imaging system, a magnetic resonance imaging system, a proton computed tomography imaging system and a positron emission tomography imaging system.

6. The radiotherapy system according to claim 1, wherein the particle beam control system, during a radiation treatment session, is arranged to lock the beam intersect region to a predetermined position within the radiation target.

7. The radiotherapy system according to claim 1, wherein the particle beam control system, during a radiation treatment session, is arranged to sweep the beam intersect region across the radiation target along a predetermined path.

8. The radiotherapy system according to claim 1, wherein the particle beam control system, during a radiation treatment session, is arranged to stepwise reposition the beam intersect region to predetermined position within the radiation target.

9. The radiotherapy system according to claim 1, wherein the particle beams are proton beams.

* * * * *